United States Patent
Breguet

(10) Patent No.: US 7,704,075 B2
(45) Date of Patent: Apr. 27, 2010

(54) INSTRUMENT FOR DRILLING RADICULAR CHANNELS

(75) Inventor: Olivier Breguet, Le Locle (CH)

(73) Assignee: Jean-Claude Rouiller, La Chaux-de-Fonds (CH)

( * ) Notice: Subject to any disclaimer, the term of this patent is extended or adjusted under 35 U.S.C. 154(b) by 295 days.

(21) Appl. No.: 10/554,148

(22) PCT Filed: Apr. 20, 2004

(86) PCT No.: PCT/CH2004/000239
§ 371 (c)(1), (2), (4) Date: Oct. 21, 2005

(87) PCT Pub. No.: WO2004/093712
PCT Pub. Date: Nov. 4, 2004

(65) Prior Publication Data
US 2007/0082318 A1    Apr. 12, 2007

(30) Foreign Application Priority Data
Apr. 24, 2003 (FR) .................. 03 05019

(51) Int. Cl.
*A61C 5/02* (2006.01)
(52) U.S. Cl. .................... 433/102
(58) Field of Classification Search ......... 433/65–66, 433/102, 81, 224; 606/80; D15/139; 175/334, 175/394; 264/116
See application file for complete search history.

(56) References Cited

U.S. PATENT DOCUMENTS

| | | | |
|---|---|---|---|
| 1,198,690 A * | 9/1916 | Barton ............... | 175/420 |
| 2,861,341 A * | 11/1958 | Bjorklund ............. | 433/165 |
| 4,260,379 A | 4/1981 | Groves et al. | |
| 4,538,989 A | 9/1985 | Apairo, Jr. et al. | |
| 5,876,202 A * | 3/1999 | Berlin ............... | 433/102 |
| 6,074,209 A | 6/2000 | Johnson | |
| 2002/0182565 A1 * | 12/2002 | Senia et al. ........... | 433/102 |

FOREIGN PATENT DOCUMENTS

CH    513 640    10/1971

(Continued)

OTHER PUBLICATIONS

Machine translation of CH 513, 640 by EPO Nov. 2, 2007. http://v3.espacenet.com/textdes?DB=EPODOC&IDX=CH513640&F=0&QPN=CH513640.*

*Primary Examiner*—Cris L Rodriguez
*Assistant Examiner*—Heidi M Eide
(74) *Attorney, Agent, or Firm*—Davis & Bujold, P.L.L.C.

(57) ABSTRACT

The drilling instrument (10), for cleaning and forming of radicular teeth canals, comprises an end section (11), mounted in a chuck and driven by an electric motor, a distal region (12), a central region (13), provided with cutting flutes (16) and a proximal region (14) with a rounded end (15), serving to guide the instrument in the canal. The envelope (20) around the proximal, central and distal regions has a generally inverted cone shape with a vertex angle (F) identical over the whole length thereof. The junction region (17) between the proximal region (14) and the end section (11) has an incipient fracture (18), calibrated such as to break on application of a given driving torque. The instrument eliminates all risk of jamming and hence breakage in the radicular canal.

15 Claims, 2 Drawing Sheets

FOREIGN PATENT DOCUMENTS

| | | |
|---|---|---|
| EP | 0 890 403 A1 | 1/1999 |
| GB | 916197 | 1/1963 |
| WO | WO 00/59399 | 10/2000 |
| WO | WO 01/10329 | 2/2001 |
| WO | WO 02/065938 | 8/2002 |

* cited by examiner

INSTRUMENT FOR DRILLING RADICULAR CHANNELS

This application is a national stage completion of PCT/CH2004/000239 filed Apr. 20, 2004 which claims priority from French Application Serial No. 03/05019 filed Apr. 24, 2003.

TECHNICAL DOMAIN

The present invention concerns an instrument for drilling root canals, particularly a flexible drilling instrument to be driven mechanically by an electric motor, said instrument comprising an end section for installation in a chuck driven by said electric motor, a proximal region adjacent to said end section, a central region extending from the proximal region, and a distal region extending from the central region to guide the instrument inside a root canal.

PRIOR ART

Cleaning and shaping root canals which will receive obturating material is done using drilling instruments with one active conical portion comprising one or more cutting edges arranged in a spiral along this active portion. This type of dental instrument is illustrated, for example, by U.S. Pat. No. 4,260,379 and International Publication No. WO 00/59399. Given the fact that root canals are rarely straight and often quite curved, drilling instruments, also known as endodontic files, must be flexible. This is why the material used for fabricating the instruments has now been changed from stainless steel to titanium-nickel.

Endodontic files may be designed for either manual use or mechanized use. When they are driven by an electric motor, it is compulsory to use titanium-nickel because of the cyclical wear that appears over the course of use in curved canals. With the continuous rotation technique, the file turns at a low speed (for example, between 100 and 2,000 rotations per minute) and advances through the opening in the canal. The active region on the file cuts or scrapes the walls of the root canal. This region, which is short at the beginning of the intervention, extends farther and farther as the file advances through the canal. More and more drive torque must be applied to the file in order to overcome the increasing friction forces and make the file turn at the desired speed as it advances. The farther the file progresses into the canal, the greater the risk of it becoming blocked or jammed. When this occurs, the torque applied to the file increases sharply, risking file breakage. Having a file break in the root canal is an event a dentist dreads, as the broken point is usually irretrievable.

In addition, the instruments currently available on the market for use with the new technique of driving files mechanically derive directly from traditional spiral shaped instruments, specifically those described in Patents CH 513 640 and U.S. Pat. No. 4,538,989. It is precisely because of this spiral shape that the jamming and blocking occurs, inevitably terminating in a broken instrument.

In order to avoid this undesirable jamming/blocking phenomenon, the manufacturers of endodontic instruments have proposed some solutions.

One of these solutions consists of blunting the cutting edges on the instrument to a greater or lesser extent to prevent them from gashing the material and boring a passageway either through the substance inside the canal or the substance forming the canal walls. Another solution consists of providing a large concentric area called a radian plane. These technologies are illustrated in U.S. Pat. No. 6,074,209.

The tendency toward jamming is at least partially eliminated through a method of working called the "crown down" method, which consists of forming the root canal using instruments that taper to varying degrees, beginning with the most tapered instruments. In this way the frictional forces that impose such restraints are limited to a short region of the active portion of the instrument and prevent it from becoming "encased."

These approaches have often been shown to be ineffective to prevent stalling and in addition, they reduce the effectiveness of the cutting function of the instrument, thus leading to increased working torque and risk of breakage.

Considering the above disadvantages and risks related to these new working methods, it becomes apparent that the gain in time over traditional methods is practically nil. Furthermore, the practitioner's work remains delicate, demanding a certain dexterity to avoid the risks of stalling/blocking and the consequences such an accident might have for the patient.

Nevertheless, certain improvements made to the instruments demonstrate that the mechanically driven drilling method may lead to shorter working time and greater working comfort, while also improving the quality of the work performed because the natural trajectory of the canal is followed. The improvements must provide for observation of cyclical wear on the instruments, regulation of frictional forces, and prevention of stalling that leads to instrument blockage and may cause breakage.

To prevent wear on the metal that forms the instruments, called cyclical wear, the most reliable method would doubtless be one-time use of instruments. However, this measure would not be very economical and certainly not justifiable from a technical viewpoint, since cyclical wear varies according to the curve of the canal where the intervention takes place. In addition, each instrument is subject to a different amount of wear depending on its size, the extent to which it tapers, working torque, and rotation speed.

Publication WO 01/10329 describes a method for marking instruments permitting indexes of successive wear to accumulate after the instrument has been used several times. This simple method is very effective and constitutes a reliable tool for evaluating cyclical wear over the life of a tool such as an endodontic type file. It offers a way of regulating wear on the metal while simultaneously recording the "lifespan" of the instrument and storing the information until it is finally discarded.

Higher and higher torque must be applied to the file as it progresses through the canal. To limit the risk of stalling, International Publication No. WO 02/065938 describes a drilling instrument with a specific helical shape. Each file has three or four cutting edges that cut all along the active portion. Each edge describes an undulating, helical trajectory inside a tapered envelope. In this way, no cutting edge is in continuous contact with the tapered envelope, but only at certain specific points, eliminating a considerable increase in drive torque on the instrument as it penetrates deeper inside the root canal. Because of this, the frictional forces are considerably weaker and stalling can be avoided by precisely selection of the various paths and helical angles of the instruments along the active instrument portion. Another way to avoid stalling is to use an instrument comprising a spiral with alternating steps such as the one described in European Publication No. EP 0 890 403 A1.

Nevertheless, in actuality, a certain number of instruments break during use. Analysis of the cause of breakage leads to the conclusion that many instances of instrument breakage are due to failure to respect the rules of use; that is, regulating the parameters and modes of use, which are as follows:

Working speed (rotations/minute by the instrument);
Apical pressure;
Back-and-forth motion;
Length of time worked;
Wear on metal;
Progression.

Instrument rotation speed while working (100 to 2,000 rotations per minute) is easily regulated by using the new motor/counter-angle units proposed by numerous manufacturers.

The apical pressure to be applied can vary enormously from one type of instrument to another and also from one instrument reference to another within the same series. With certain instruments that have a very strong tendency to stall, pressure is in fact a restraining force. With certain known instruments, the pressure the operator must exert in order to progress steadily is comparable to the pressure exerted to write on paper with a pencil. The back-and-forth motion evacuates debris and prevents the wear on the instrument caused by the pressure it is subjected to from being confined to the same area on the instrument. The rule to apply is to never remain in a stationary position within the canal. The efficiency of the instruments described above shortens working time and thus decreases wear on the metal.

Progression by the instrument from the beginning to the end of the canal must occur in such a way that the instrument removes a reasonable quantity of material with each revolution and that the debris is thoroughly evacuated. The higher the speed of progression for a given rotation speed, the more important it is to remove a sufficient amount of material per rotation. Obviously there is a limit to the speed of progression for a given rotation speed. This limit is often difficult for the practitioner to evaluate because he has in his hands a motorized counter-angle type instrument that is super powerful in relation to the resistance of endodontic files. With this equipment the practitioner does not have the much appreciated sensitivity associated with manual instruments.

With proper training, it is possible for practitioners to easily master certain parameters specified above. However, it is difficult to give precise rules for use concerning apical pressure and speed of progression. During demonstrations, experiments are performed using blocks of plastic material and it has been shown that some people have a certain mechanical sense and a certain sensitivity that prevent them from exceeding the limits of resistance in the material. Others, however, do not possess these qualities and do not perceive the resistance of the materials, overestimating how much work the file must perform in a given time span. The fact of using a mechanically driven tool, a super powerful counter-angle that can drill holes in metal does not facilitate this perception.

In an attempt to overcome these disadvantages, the manufacturers of motorized devices have developed a new type of motor with torque control. This control allows the file rotation to be stopped when the working torque becomes too high.

While the idea seems worthwhile at the outset, in practice, the expectation of increased safety when using motors with torque control proves to be misleading and even dangerous.

In actuality, all endodontic instruments used for cleaning root canals are tapered. They generally taper for between 2% and 12%. It should also be specified that according to statistics, most instrument breakage occurs along the first third of the length of the file from the point. In practice, it is observed that drive systems with torque control offer only a partial solution. Actually, for utmost safety, the maximum torque delivered by the drive system, called a counter-angle system, should correspond to the breakage torque at the tip of the instrument. If the counter-angle is programmed on the basis of the value of this torque, which is very low, the practitioner becomes unable to work because the motor becomes blocked when the instrument is engaged at a certain depth within the canal. This blockage occurs more or less rapidly depending upon the conicity of the instrument and the cutting power of the instrument. For work to remain possible, the working torque must be increased greatly, especially for instruments with low cutting power. For this reason, in practice, due to regulation of the torsion torque limit, the instruments are in most cases unprotected against breakage due to torsion up to the first half of their active portion. There may be even less protection with progressively tapered instruments.

In order for the mechanically driven rotary drilling method to become universally adopted by general dental practitioners and not just endodontic specialists, it is necessary to further reduce the incidence of "instrument breakage" due to the causes enumerated previously. To achieve this, it is imperative to fulfill the following conditions:

working torque must correspond to breaking torque at the level of the instrument tip;
the risk of stalling must be reduced to nothing;
the risk of embedding must be reduced to nil;
regulation of wear on the material used for the instrument must be ensured;
the instrument must be used according to an established standard sequence;
the tip of the instrument must be guided.

DESCRIPTION OF THE INVENTION

The present invention proposes overcoming the disadvantages mentioned above and fulfilling the conditions outlined with a method for mechanically driven rotary drilling that provides a reliable, universal solution which not only improves the quality of work performed by the practitioner, but also eliminates risks to the patient, all under favorable economic conditions.

This goal is achieved by the instrument of the invention as defined in the preamble, characterized in that the envelope in the proximal, central and distal regions has a generally inverted cone shape, with the wider portion corresponding to the distal region and the smaller portion corresponding to the proximal region.

According to a first mode of embodiment, said envelope is shaped like a truncated cone and the vertex angle is the same for the entire length.

According to a second embodiment, said envelope consists of several juxtaposed portions extending axially from one another, said portions each being cone shaped and each truncated portion having a different vertex angle, with the angle at the largest tip corresponding to the distal region, the angle at the smallest tip corresponding to the proximal region, and the angles at the intermediate tips corresponding to the central region.

According to a third embodiment, the angle of the envelope in relation to the axis of the instrument decreases progressively and regularly from the distal region to the proximal region.

Preferably, there is a junction region on the instrument between said proximal region and said end section, said junction region comprising a slight break calibrated to split when a predetermined drive torque is applied.

According to a first design, said break consists of a segment that is reduced in section.

According to a second design, the break consists of a modification in the type and/or structure of the instrument material.

According to a third design, the break consists of at least one peripheral notch formed in said junction region. The predetermined drive torque preferably corresponds to the breaking torque in the distal region of the instrument.

To facilitate guiding the instrument, said distal region advantageously comprises a rounded point.

According to a particularly advantageous design, said central region has a polygonal section and comprises sharp fluted cutting edges that are generally helical.

According to a variation, said active central region may be polygonal and comprise blunt fluted cutting edges that are generally helical.

In a very advantageous embodiment, said central region comprises working sections and non-working sections, with the non-working sections being smaller in section than the working sections.

According to another variation, said central region comprises helical sections and rectilinear sections.

SUMMARY DESCRIPTION OF THE DRAWINGS

The principal advantages of the present invention will be more readily apparent from the description of various embodiments with reference to the attached drawings, in which.

HOW TO ACHIEVE THE INVENTION

Figure 1:
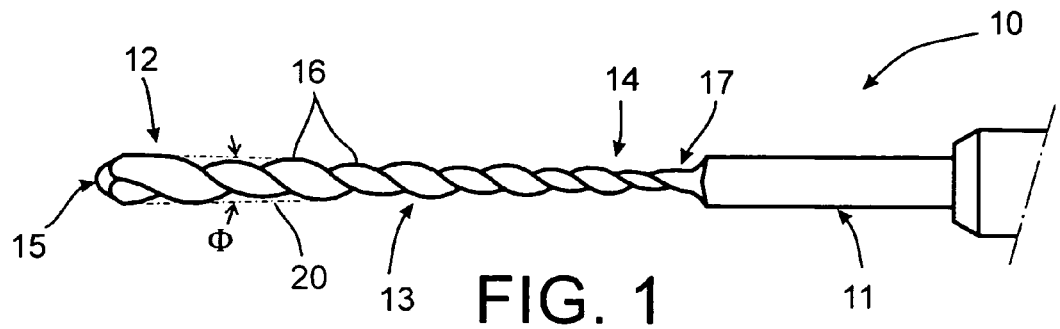
FIG. 1 represents a view of a first embodiment of the instrument according to the invention.

With reference to the drawings, the instrument 10 that is shown comprises, in all the embodiments, an end section 11 to be attached to a chuck driven by an electric motor (not shown), a distal region 12, a central region 13 and a proximal region 14. The distal region, located opposite end section 11, guides the instrument through a root canal. This region terminates in a rounded extremity 15 to efficiently and steadily guide the instrument while preventing the instrument from becoming embedded in the canal walls, thereby blocking its progression. In the examples shown in FIGS. 1 and 2, central region 13 is polygonal and comprises flutes 16 with sharp cutting edges that are generally helical. In the examples shown in FIGS. 3 and 4, central region 13 is polygonal and comprises flutes 16 having helical portions 16a alternating with rectilinear portions 16b. This alternating pattern reduces the tendency of the instrument to stall. The flutes may be sharp or blunt, depending upon their use. The two embodiments are used according to the nature of the work to be performed or the work habits of the dental practitioner.

In the examples shown in FIGS. 1 through 4, envelope 20 for distal regions 12, central region 13 and proximal region 14 is generally shaped like an inverted cone, with the portion having the widest section corresponding to distal region 12 and the smallest section, to proximal region 14. In all these examples, this envelope is shaped like a truncated cone and has a vortex angle $\Phi$ that is identical along its entire length.

Figure 5:
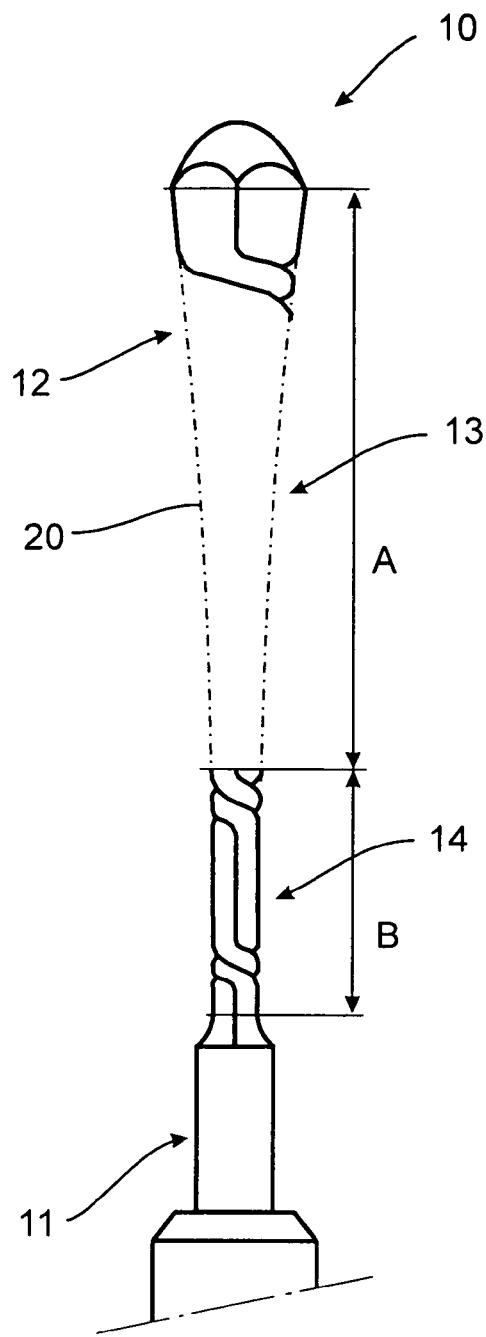
FIG. 5 represents a schematic view illustrating a specific embodiment of the instrument according to the invention.

In the exemplary embodiment illustrated in FIG. 5, the angle of envelope 20 relative to the axis of instrument 10 decreases progressively and regularly from distal region 12 to proximal region 14. Instrument 10 comprises a section A that includes distal region 12 and central region 13, and a section B that essentially corresponds to the proximal region attached to end section 11. According to one possible embodiment, the portion of envelope 20 that corresponds to section B may have a constant section, that is, it may be cylindrical in shape. However, according to the most current embodiment, the regular variation of the angle at the center extends for the entire length of the envelope. In other words, the inverse cone has a vortex angle that increases progressively from the proximal region to the distal region.

Figure 6:
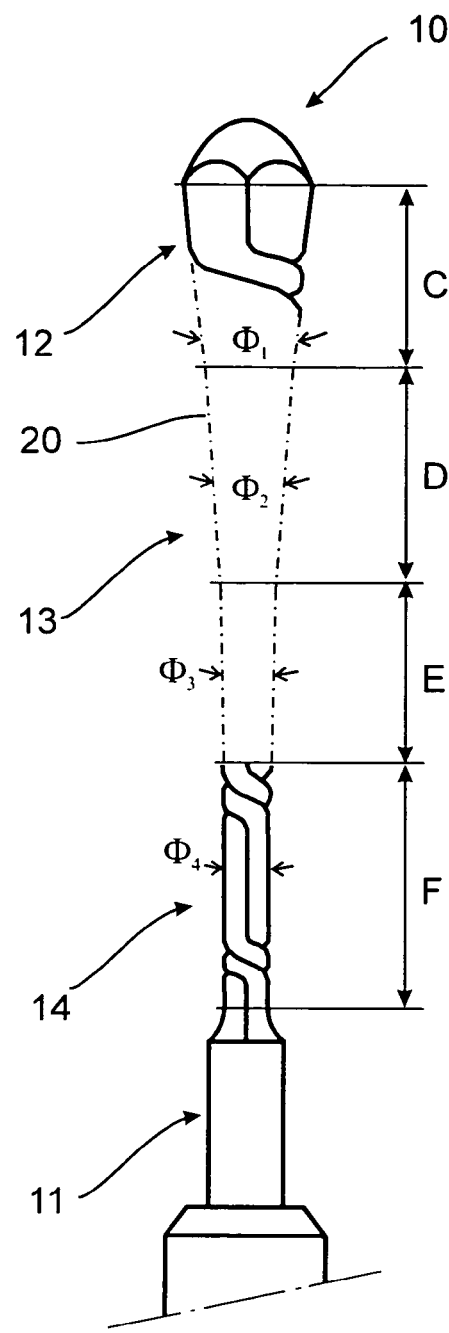
FIG. 6 represents a schematic view illustrating another specific embodiment of the instrument according to the invention.

In the exemplary embodiment shown in FIG. 6, the envelope consists of several sections C, D, E and F juxtaposed and extending axially from one another, said sections each being generally cone shaped, with each of the cones having a different vortex angle $\Phi_1$, $\Phi_2$, $\Phi_3$, and $\Phi_4$ with the largest vortex angle $\Phi_1$ corresponding to distal region 12, the smallest vortex angle $\Phi_4$ corresponding to the proximal region 14 and the intermediate vortex angles $\Phi_2$, $\Phi_3$, corresponding to central region 13.

In all the examples shown, instrument 10 comprises a junction region 17 between said proximal region 14 and said end section 11, said junction region 17 comprising a partial break calibrated to split when a predetermined drive torque is applied.

Figure 2:
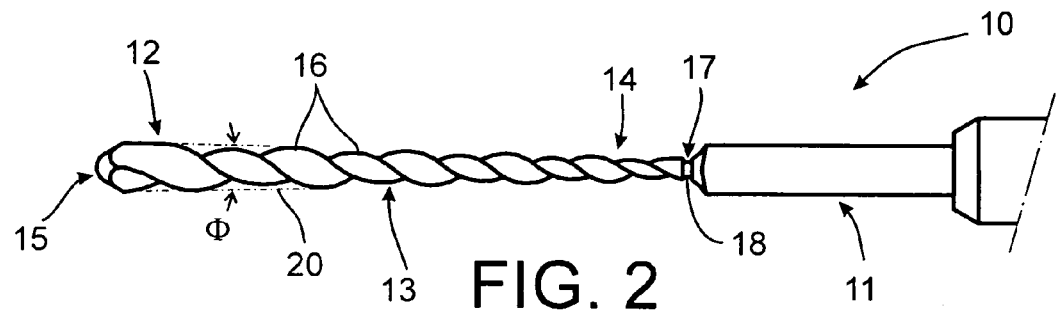
FIG. 2 represents a view of a second embodiment of the instrument according to the invention.
Figure 3:
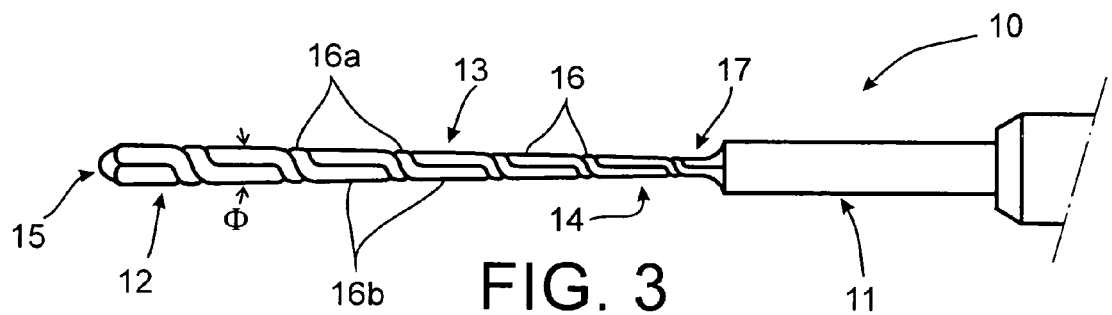
FIG. 3 represents a view of a third embodiment of the instrument according to the invention.

In the exemplary embodiments shown in FIGS. 1 through 3, for example, said partial break consists of a portion with reduced section in the area of junction region 17. The reduced section may be formed by the appropriate machining technique when the instrument is shaped, particularly flutes 16 with cutting edges on central region 13 of the instrument.

Figure 4:
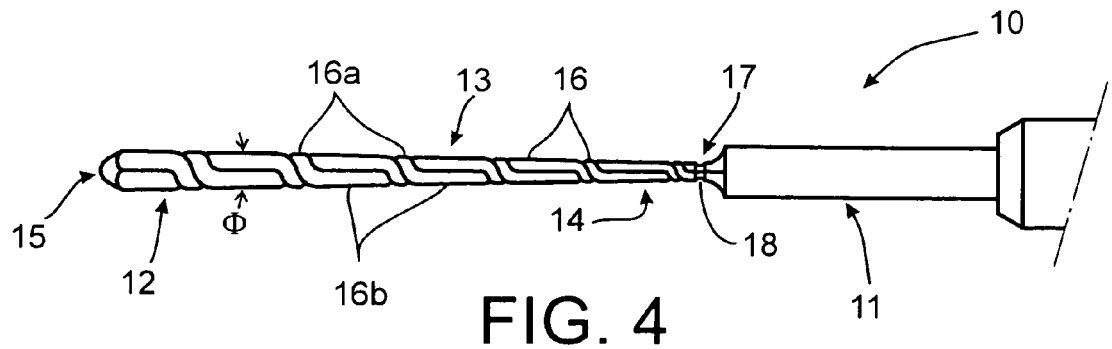
FIG. 4 represents a view of a fourth embodiment of the instrument according to the invention.

In the embodiments shown in FIGS. 2 and 4, said partial break in junction region 17 may be formed by machining at least one peripheral notch 18, preferably formed when the instrument is shaped, particularly flutes 16 with cutting edges on the instrument.

The partial break in junction region 17 could also be made by modifying the structure or the type of material used to make the instrument.

The advantage of all these embodiments, regardless of the shape of the distal, central and proximal regions, is that if the prescribed torque for the counter-angle is exceeded, the instrument breaks just at the end of the active portion in a place that is accessible to the practitioner, allowing it to be recovered from the canal without any problem. Even if it breaks because of misuse, the practitioner can always retrieve it without causing any irreversible damage.

The width of the angle of the inverse cone, various shapes of which have been described above, may vary depending upon the instrument. It is possible to make a series of instruments with wider or smaller angles. The instruments illustrated in FIGS. 1 and 2, in particular, have flutes shaped to push the debris toward the outside of the canal and which are also adapted to overcome blocking or jamming. The inverse cone principle may advantageously be applied to root canal drilling instruments of any type whatsoever. There may be any number of flutes, of any shape, with any cutting angle. The principle adapts particularly well to motor driven tools using counter-angles.

It will be noted that the root canal must be conical at the end of its preparation for the obturating material. The reverse cone shape of the instrument described above is designed for use at only one specific point in time during the preparation sequence, specifically, the first passage, in order to secure the passage for the conical instruments. It forms a complementary part of a series of treatment instruments and is used to perform preparatory work while eliminating the risk of jamming and breaking.

The invention claimed is:

1. A flexible dental instrument for use in drilling a root canal, and the dental instrument being designed to be mechanically driven by an electric motor, the dental instrument (10) being flexible and comprising:

an end section (11) for mounting in a chuck driven by an electric motor,
   a proximal region (14) adjacent to said end section (11),
   a central region (13) extending from said proximal region, and
   a distal region (12) extending from said central region (13) for guiding the instrument through a root canal, and
   an envelope (20) comprising the proximal region, the central region and the distal region and the envelope defining an axial length and having a generally inverted cone shape, with a widest portion of the envelope (20) corresponding to the distal region (12) and a smallest portion of the envelope (20) corresponding to the proximal region (14),
   wherein the dental instrument further comprises a junction region (17), located between the proximal region (14) and the end section (11), and the junction region (17) comprises an area of the envelope (20) having a minimum thickness which is designed to break in the event that a predetermined drive torque is applied to the envelope (20) during use of the dental instrument, and a leading end of the end section (11) tapers toward and joins with the junction region (17), and
   the central region (13) is polygonal and comprises hollowed flutes (16) with sharp cutting edges that are generally helical.

2. The dental instrument according to claim 1, wherein the envelope (20) has a truncated cone shape and comprises a vortex angle ($\Phi$) that is identical along its entire length.

3. The dental instrument according to claim 1, wherein the envelope (20) consists of several juxtaposed sections (C, D, E, F) extending axially from one another, each of said sections having a truncated cone shape and each of said truncated cones comprising a different vortex angle ($\Phi_1$, $\Phi_2$, $\Phi_3$, and $\Phi_4$), with a widest vortex angle ($\Phi_1$) corresponding to the distal region (12), a smallest vortex angle ($\Phi_4$) corresponding to the proximal region (14), and at least one intermediate vortex angles ($\Phi_2$, $\Phi_3$) corresponding to the central region (13).

4. The dental instrument according to claim 1, wherein an angle of the envelope (20) relative to an axis of the dental instrument decreases progressively and regularly from the distal region (12) to the proximal region (14).

5. The dental instrument according to claim 1, wherein the area of the envelope (20) which is designed to break consists of a reduced section adjacent the proximal region (14) of the envelope (20).

6. The dental instrument according to claim 1, wherein the area of the envelope (20) which is designed to break consists of a modification in one or more of type and structure of material used for the dental instrument.

7. The dental instrument according to claim 1, wherein the area of the envelope (20) which is designed to break consists of at least one peripheral notch (18) formed in said junction region (17).

8. The dental instrument according to claim 1, wherein the predetermined drive torque corresponds to a torque at which the distal region of the dental instrument breaks.

9. The dental instrument according to claim 1, wherein the distal region (12) comprises a rounded tip.

10. A flexible dental instrument for use in drilling a root canal, and the dental instrument being designed to be mechanically driven by an electric motor, the dental instrument (10) being flexible and comprising:

an end section (11) for mounting in a chuck driven by an electric motor,
    a proximal region (14) adjacent to said end section (11),
    a central region (13) extending from said proximal region, and
    a distal region (12) extending from said central region (13) for guiding the instrument through a root canal, and
    an envelope (20) comprising the proximal region, the central region and the distal region and the envelope defining an axial length and having a generally inverted cone shape, with a widest portion of the envelope (20) corresponding to the distal region (12) and a smallest portion of the envelope (20) corresponding to the proximal region (14),
    wherein the dental instrument further comprises a junction region (17), located between the proximal region (14) and the end section (11), and the junction region (17) comprises an area of the envelope (20) having a minimum thickness which is designed to break in the event that a predetermined drive torque is applied to the envelope (20) during use of the dental instrument, and a leading end of the end section (11) tapers toward and joins with the junction region (17), and
    the central region (13) is polygonal and comprises flutes (16) with blunt edges that are generally helical.

11. A flexible dental instrument for use in drilling a root canal, and the dental instrument being designed to be mechanically driven by an electric motor, the dental instrument (10) being flexible and comprising:

an end section (11) for mounting in a chuck driven by an electric motor,
    a proximal region (14) adjacent to said end section (11),
    a central region (13) extending from said proximal region, and
    a distal region (12) extending from said central region (13) for guiding the instrument through a root canal, and
    an envelope (20) comprising the proximal region, the central region and the distal region and the envelope defining an axial length and having a generally inverted cone shape, with a widest portion of the envelope (20) corresponding to the distal region (12) and a smallest portion of the envelope (20) corresponding to the proximal region (14),
    wherein the dental instrument further comprises a junction region (17), located between the proximal region (14) and the end section (11), and the junction region (17) comprises an area of the envelope (20) having a minimum thickness which is designed to break in the event that a predetermined drive torque is applied to the envelope (20) during use of the dental instrument, and a leading end of the end section (11) tapers toward and joins with the junction region (17), and
    the central region (13) comprises helical sections (16a) and rectilinear sections (16b).

12. A flexible dental instrument for drilling a root canal, the dental instrument being manufactured from titanium-nickel and being flexible and designed to be mechanically driven by an electric motor, the flexible dental instrument (10) comprising:

a end section (11) for mounting in a chuck of an electric motor;

a proximal region (14) adjacent to the end section (11);

a central region (13) extending from the proximal region; and a distal region (12) extending from the central region (13) for guiding the dental instrument through a root canal, and the distal region (12) terminating in a rounded tip;

an envelope (20) comprising only the proximal region, the central region and the distal region and the envelope (20) defining an axial length and having a generally inverted cone shape with a widest portion of the envelope (20) corresponding to the distal region (12) and a narrowest portion corresponding to the proximal region (14);

wherein the dental instrument further comprises a junction region (17), located between the proximal region (14) and the end section (11), and the junction region (17) comprises an area, with a minimum thickness, which is designed to break when a predetermined drive torque is applied to the envelope (20), and a leading end of the end section (11) tapers toward and joins with the junction region (17); and the distal region (12), the central region (13) and the proximal region (14) have a polygonal cross section and comprise a plurality of hollow flutes with helical cutting edges.

13. The dental instrument according to claim 12, wherein the area which is designed to break comprises one of:

a reduced section adjacent the proximal region (14) of the envelope (20);

a modification in one or more of type and structure of material used for the dental instrument; and at least one peripheral notch (18) formed in the junction region (17).

14. A flexible root canal dental instrument for drilling a root canal, the dental instrument being manufactured from titanium-nickel and being flexible and designed to be mechanically driven by an electric motor, the flexible dental instrument (10) comprising:

a cylindrical end section (11) for mounting in a chuck of an electric motor;

a proximal region (14) adjacent to the end section (11);

a central region (13) extending from the proximal region; and a distal region (12) extending from the central region (13) for guiding the dental instrument through a root canal, and the distal region (12) terminating in a rounded tip which, during use, guides the dental instrument and minimizes the possibility of the dental instrument becoming embedded in a canal wall of a tooth;

an envelope (20) comprising the proximal region, the central region and the distal region and the envelope (20) defining an axial length and having a generally inverted cone shape with a widest portion of the envelope (20) corresponding to the distal region (12) and a smallest portion corresponding to the proximal region (14);

wherein the dental instrument further comprises a junction region (17), located between the proximal region (14) and the end section (11), and the junction region (17) comprises an area, with a minimum thickness, which is designed to break when a predetermined drive torque is applied to the envelope (20) and a vertex angle is constant along the entire axial length of the envelope (20), and a leading end of the end section (11) tapers toward and joins with the junction region (17); and the distal region (12), the central region (13) and the proximal region (14) have a polygonal cross section and comprise a plurality of hollow flutes with helical cutting edges.

15. The dental instrument according to claim 14, wherein the area which is designed to break comprises one of:

a reduced section adjacent the proximal region (14) of the envelope (20);

a modification in one or more of type and structure of material used for the dental instrument; and at least one peripheral notch (18) formed in the junction region (17).

* * * * *